United States Patent [19]

Hodo et al.

[11] Patent Number: 4,676,110
[45] Date of Patent: Jun. 30, 1987

[54] FATIGUE TESTING A PLURALITY OF TEST SPECIMENS AND METHOD

[75] Inventors: James D. Hodo; Dennis R. Moore; Thomas F. Morris, all of Huntsville; Newton G. Tiller, Athens, all of Ala.

[73] Assignee: The United States of America as represented by the Administrator of the National Aeronautics and Space Administration, Washington, D.C.

[21] Appl. No.: 886,121

[22] Filed: Jul. 16, 1986

[51] Int. Cl.$^4$ ............................................. G01N 3/32
[52] U.S. Cl. .......................................... 73/809; 73/810
[58] Field of Search ................. 73/808, 809, 810, 811, 73/806, 816, 826, 831, 834, 856, 798; 374/47

[56] References Cited

U.S. PATENT DOCUMENTS

| | | | |
|---|---|---|---|
| 2,356,763 | 8/1944 | Keinath | 73/809 |
| 3,065,632 | 11/1962 | Crane et al. | 73/810 |
| 3,304,768 | 2/1967 | Naumann et al. | 73/816 |
| 3,491,586 | 1/1970 | Branger | 73/809 |
| 3,793,880 | 2/1974 | Sugi et al. | 73/811 |
| 3,937,071 | 2/1976 | Slota et al. | 73/810 |

Primary Examiner—Stewart J. Levy
Assistant Examiner—Robert R. Raevis
Attorney, Agent, or Firm—Joseph H. Beumer; John R. Manning; Leon D. Wofford, Jr.

[57] ABSTRACT

A fatigue testing apparatus (10) for simultaneously subjecting a plurality of material test specimens (24) to cyclical tension loading to determine the fatigue strength of the material. The fatigue testing apparatus includes a pulling head (12) having cylinders (26) defined therein which carry reciprocating pistons (32). The reciprocation of the pistons is determined by cyclical supplies of pressurized fluid to the cylinders. Piston rods (18) extend from the pistons through the pulling head and are attachable to one end of test specimens, the other end of the test specimens being attachable to a fixed base (38), causing test specimens attached between the piston rods and the base to be subjected to cyclical tension loading. Because all of the cylinders share a common pressurized fluid supply, the breaking of a test specimen does not substantially affect the pressure of the fluid supplied to the other cylinders nor the tension applied to the other test specimens.

15 Claims, 2 Drawing Figures

FATIGUE TESTING A PLURALITY OF TEST SPECIMENS AND METHOD

ORIGIN OF THE INVENTION

The invention described herein was made by employee(s) of the United States Government and may be manufactured and used by or for the Government for governmental purposes without the payment of any royalties thereon or therefor.

BACKGROUND OF THE INVENTION

The present invention relates to an apparatus for simultaneously subjecting a plurality of material test specimens to cyclical tension loading to determine the fatigue strength limit of the material.

When specifying a particular material for a specific application, it becomes important to know the various material characteristics of the materials available. Typically, the materials are run through a battery of tests to determine these characteristics. One such characteristic which is often tested is the fatigue strength of the material.

Determining the fatigue strength of the material entails subjecting a representative specimen of the material to cyclical tension loading until the specimen breaks. The limiting stress created by the tension loading at which the specimen breaks is the fatigue strength limit of the material. In order to achieve an accurate statistical evaluation, a large number of specimens are tested.

Normally, testing of the material is accomplished by testing one specimen at a time in a conventional fatigue testing apparatus. This can be a very time consuming process as each specimen has to be tested one by one. Various devices have been patented which enable several specimens to be tested at one time. One such device was patented in U.S. Pat. No. 3,491,586, granted to Branger, which discloses a fatigue testing apparatus for subjecting a plurality of test specimens to alternating tension and compression loads through use of hydraulically actuated cylinders. Another such device was patented in U.S. Pat. No. 4,030,348, granted to Fletcher et al., which discloses a machine for use in monitoring fatigue life for the plurality of elastomeric specimens through use of a reciprocating drive train. Still another multiple specimen fatigue testing device was patented in U.S. Pat. No. 3,937,071, granted to Slota et al., which discloses the use of a plurality of test stations each having an air actuated tensioning piston attached to a test specimen. While the above patented devices may perform satisfactorily, they are relatively complex in configuration.

Accordingly, an object of the present invention is to provide a device for simultaneously subjecting a plurality of test specimens to cyclical tension loading which is relatively simple in configuration.

Another object of the present invention is to provide a device and method for simultaneously subjecting a plurality of test specimens to cyclical tension loading which, upon the breaking of a specimen, allows for the cyclical tension loading of the remaining specimens to be substantially unchanged and continued.

Still another object of the present invention is to provide a device for simultaneously subjecting a plurality of test specimens to cyclical tension loading which applies substantially equal tension loads to all of the specimens being tested.

SUMMARY OF THE INVENTION

The above objectives are accomplished according to the invention by a fatigue testing apparatus which includes a pulling head having a plurality of piston rods extending therefrom. The piston rods are attached to pistons which are carried in cylinders defined in the pulling head. Upon introduction of pressurized fluid to the pulling head, the pressurized fluid is delivered to the cylinders via fluid passages defined in the pulling head. The delivery of the pressurized fluid to the cylinders causes the pistons carried therein to advance, which accordingly causes the piston rods to advance also. Test specimens are attached between the ends of the piston rods and a fixed surface. Advancement of the pistons due to the introduction of pressurized fluid to the cylinders and pulling head causes pulling and tension load to be placed on the specimens.

BRIEF DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Generally, the present invention includes a fatigue testing apparatus for simultaneously subjecting a plurality of testing specimens to cyclical tension loading to determine the fatigue strength limit of the test specimens. The fatigue testing apparatus comprises; a pressurized fluid source and a unique pulling head having pressurized fluid passage means for allowing pressurized fluid from the pressurized fluid source to be supplied to and exhausted from the pulling head. A plurality of cylinders are formed in the pulling head having two ends, one of the two ends is in communication with the pressurized fluid passage means and the other of the two ends has a vent defined therein. A plurality of substantially cylindrical pistons are carried in the plurality of cylinders for movement towards the vent upon the pressurized fluid passage means being supplied pressurized fluid.

A test specimen attachment mean is associated with each piston which attaches to one of the two ends of test specimen and to a corresponding piston. Fixed attachment means opposite the test specimen attachment means is provided for affixing and attaching the other of the two ends of each of the plurality of test specimens with respect to the movement of the plurality of the pistons Control means allows pressurized fluid to be alternately supplied to and exhausted from the pressurized fluid passage means in a manner that the plurality of pistons and the test specimen attachment means associated therewith move towards and away from the affixed attachment means. The movement of the test specimen attachment means towards and away from the affixed attachment means allows the plurality of test specimens to be subjected to cyclical tension loading.

Figure 1:
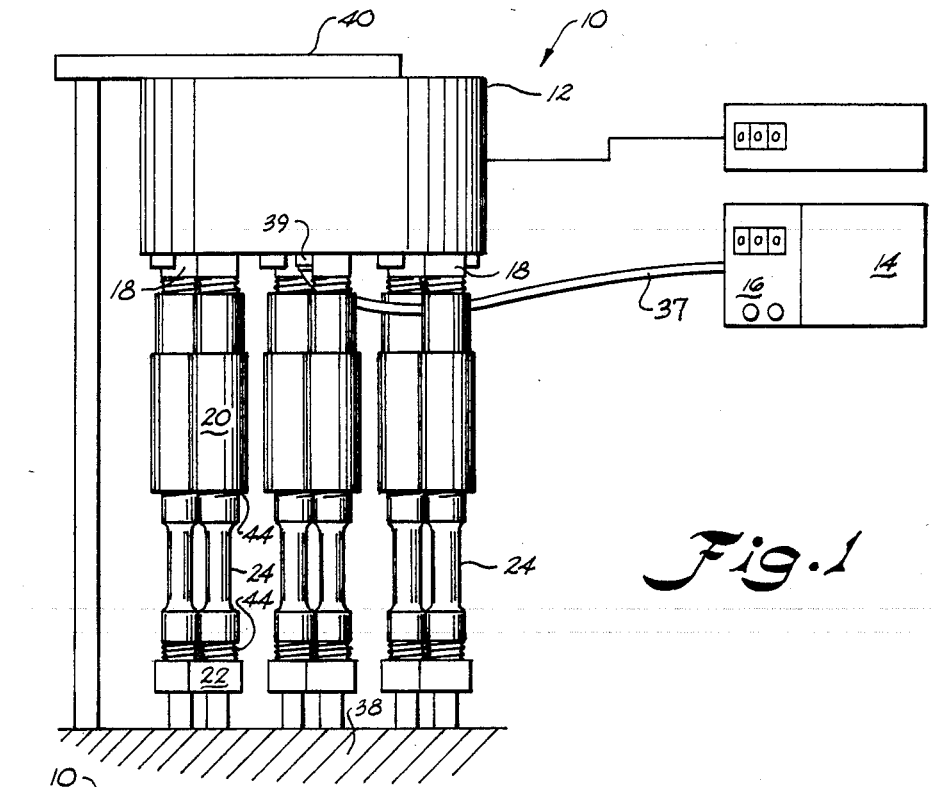
FIG. 1 is a side elevation view of a preferred form of fatigue testing apparatus constructed in accordance with the present invention.

Referring to the drawings in detail, wherein like reference characters represent like elements through the various views, the fatigue apparatus of the present invention is designated generally as 10. Fatigue testing apparatus 10 is illustrated in FIG. 1 and includes a pulling head 12, a pressurized fluid source 14 having a control device 16 associated therewith, piston rods 18 extending from pulling head 12 and attachment couplings 20 and 22 for attaching a test specimen 24 therebetween.

Figure 2:
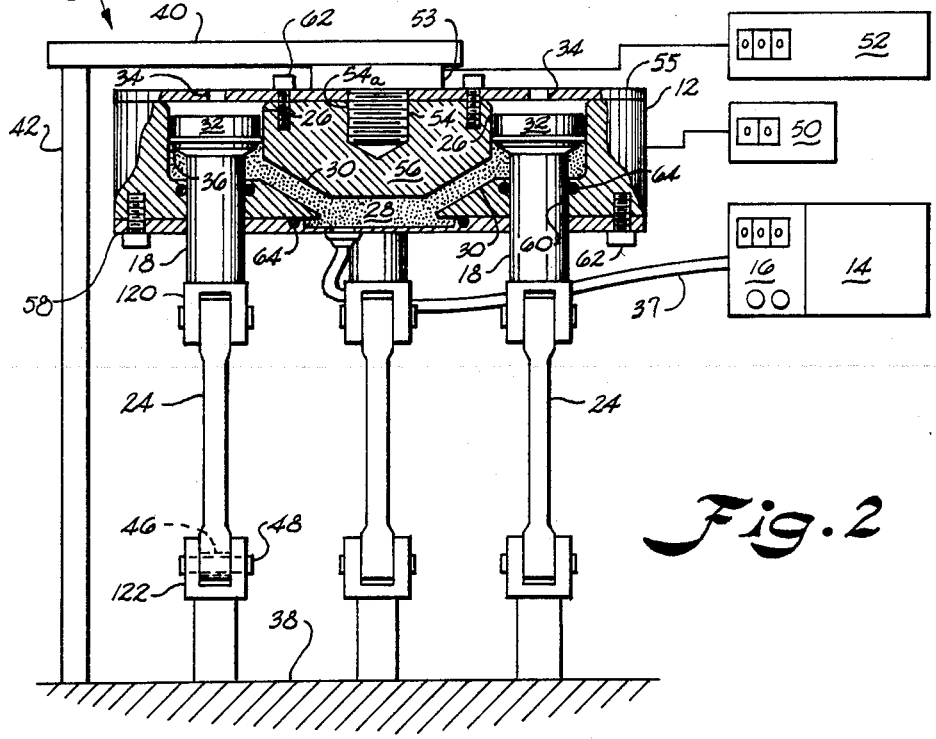
FIG. 2 is a side elevational view, with parts cut away, of a preferred form of fatigue testing apparatus constructed in accordance with the present invention.

Pulling head 12, as shown in FIG. 2, has defined therein a plurality of cylinders 26 which are in fluid communication with pressurized fluid source 14 via fluid passages 28 and 30. Carried for reciprocating movement in cylinders 26 are pistons 32. Upon introduction of pressurized fluid from pressurized fluid source 14 to fluid passages 28 and 30, pistons 32 advance in cylinders 26 towards an atmospheric vent 34 provided in the top of each cylinder 26. In other words, pressurized fluid, such as hydraulic fluid, air, etc., admitted into cylinders 26 acts on the backside 36 of pistons 32 to force pistons 32 and the piston rods 18 attached thereto towards the top of pulling head 12.

Pressurized fluid source 14 can be any suitable servo hydraulic control machine, such as a MTS 200 closed loop machine manufactured by the MTS System Corporation. Control device 16 can be any suitable conventional device which allows pulling head 12 to cyclically receive supplies of pressurized fluid. High pressure line 37 connects pressurized fluid source to pulling head 12 via coupling 39.

When it is desired to fatigue test a plurality of specimens 24, pulling head 12 is moved upwards away from a base structure 38 by means of a conventional crosshead device 40, movable by a hydraulically actuated shaft 42. There are various ways in which pulling head 12 can be moved upwards away from base structure 38 other than using the crosshead 40. For example, pulling head 12 could be provided with a simple frame structure (not shown) extending upwards from adjacent base structure 38 which would support pulling head 12 as it is moved upwards by hand or by some other conventional means.

After pulling head 12 has been moved upwards, each test specimen 24 is attached at one end thereof to a piston rod 18 by a test specimen attachment coupling 20 and at the other end to base structure 38 by a fixed attachment coupling 22. As shown in FIG. 1, attachment couplings 20 and 22 comprise internally threaded sleeves which each engage a conventional threaded end of a test specimen 24, should the test specimen have threaded ends 44. If the test specimens to be fatigue tested have conventional transverse openings 46 for attachment to fatigue testing apparatus 10, instead of threaded ends 44, then alternate embodiment attachment couplings 120 and 122 as shown in FIG. 2 can be used. Attachment couplings 120 and 122 are conventional clevis pin connections which engage a transverse opening 46 of a test specimen 24 with a pin 48.

When test specimens 24 have been attached between pistons rods 18 and base structure 38, a cyclical tension load is applied to the test specimens 24 by pressurized fluid source 14 via fluid passages 28 and 30. Pressurized fluid delivered to the cylinders 26 causes pistons 32 and the piston rods 18 attached thereto to advance away from base structure 38. This causes the test specimens to be subjected to tension loading. The pressurized fluid is applied to the pistons 32 in a cyclical manner, thus causing the test specimens 24 to be subjected to cyclical tension loading. The atmospheric vent 34 provided in the top of each cylinder 32 allows pistons 18 to relax between alternating supplies of pressurized fluid by preventing a vacuum from forming in the cylinders 26 which would tend to keep pistons 18 from setting to their lowermost position in a cylinder 26 when pressurized fluid is not being supplied. Thus, test specimens 24 are subjected to substantially no load between pressurized fluid supplies.

A conventional mechanical load cycle counter 50 is associated with the test specimens 24 for determining the number of load cycles to which each test specimen is subjected before each test specimen breaks. For this purpose, counter 50 may be connected to each specimen for counting the number of load cycles each specimen is subjected to before failure. By knowing the number of cycles and stress level at which a test specimen breaks, the fatigue strength and endurance limit, if applicable, of the material can be determined.

A conventional load cell device 52 may be used to determine the total tension load being applied to the test specimens 24 during the cyclical testing. Load cell transducers 53 could be attached to pulling head 12 using a threaded bore 54 and stud 54a provided in pulling head 12, as shown in FIG. 2.

Pulling head 12 is preferably made of steel, although any other suitable material could also be used, and is comprised of a top plate 55 having atmospheric vents 34, a center block 56 in which the fluid passages 28 and 30 and cylinders 26 are defined, and a bottom plate 58 in which piston receiving openings 60 are provided. Top plate 55 and bottom plate 58 are held to center block 56 by bolts 62. Seals 64 prevent leakage of the pressurized fluid around pistons 32 and between center block 56 and bottom plate 58.

Each cylinder 26 is connected to a central fluid passage 28, which receives pressurized fluid from pressurized fluid source 14 by a fluid channel 30. Thus, all of the cylinders 26 are in fluid communication with one another because all of the fluid channels 30 receive pressurized fluid from the same source, the central fluid passage 30.

The common pressurized fluid communication between the cylinders 26 allows for the same pressure to be simultaneously applied to all of the pistons 32, even after one of several of the test specimens 24 break during fatigue testing. Upon the breaking of a test specimen 24, the piston 32 to which the test specimen is attached advances to the uppermost position in its cylinder 26, in contact with top plate 55. Top plate 55 retains piston 32 in the cylinder when the test specimen breaks. Piston 32 is forced into contact with top plate 55 under the influence of the pressurized fluid, moving through pressurized fluid passages 28 and 30, which immediately seeks an equilibrium pressure with respect to the other pistons 32. This equilibrium pressure is substantially the same pressure as was applied to the pistons 32 before the break because the pressure of the pressurized fluid supplied from the pressurized fluid supply source 14 remains unchanged. The same pressure, and consequently the tension load applied to the remaining test specimens, remains substantially unchanged as each of the test specimens 24 sequentially or otherwise break. This feature allows a cyclical tension load of a constant magnitude to be applied to each test specimen throughout their fatigue testing.

From the foregoing, it can be seen that the above objects have been met by the fatigue testing apparatus of the present invention. While a preferred embodiment of the invention has been described using specific terms, such description is for illustrative purposes only, and it is to be understood that changes and variations may be made without departing from the spirit or scope of the following claims.

What is claimed is:

1. A fatigue testing apparatus for simultaneously subjecting a plurality of test specimens having two ends to cyclical tension loading to determine the fatigue strength limit of said plurality of test specimens, said fatigue testing apparatus comprising:

a pressurized fluid source;

a pulling head having a block containing pressurized fluid passage means formed in said block for allowing pressurized fluid from said pressurized fluid source to be supplied to and exhausted from said pulling head;

a plurality of cylinders having two ends defined in said block of said pulling head, one of said two ends being in communication with said pressurized fluid passage means and the other of said two ends having a vent to atmosphere defined therein;

a plurality of substantially cylindrical pistons carried in said plurality of cylinders for movement therein towards said vent upon said pressurized fluid passage means being supplied pressurized fluid;

test specimen attachment means associated with each of said plurality of pistons for attaching one of said two ends of said plurality of test specimens to each of said plurality of pistons;

fixed attachment means opposite said test specimen attachment means for fixedly attaching the other of said two ends of said plurality of test specimens with respect to said movement of said plurality of pistons;

control means for allowing pressurized fluid to be alternately supplied to and exhausted from said pressurized fluid passage means in a manner that said plurality of pistons and said test specimen attachment means associated therewith move towards and away from said fixed attachment means; and said movement of said test specimen attachment means allows said plurality of test specimens to be subjected to cyclical tension loading.

2. The fatigue testing apparatus defined in claim 1, further comprising piston retention means associated with said pulling head for retaining each of said plurality of pistons in said pulling head upon said fatigue strength limit being reached by said test specimens.

3. The fatigue testing apparatus as defined in claim 1, further comprising cycle counting means associated with said plurality of test specimens for determining the number of tension load cycles to which each of said test specimens is subjected before reaching said fatigue strength limit.

4. The fatigue testing apparatus as defined in claim 1, wherein said test specimen attachment means and said fixed attachment means comprise threaded connections.

5. The fatigue testing apparatus as defined in claim 1, wherein said test specimen attachment means and said fixed attachment means comprise clevis pin connections.

6. The fatigue testing apparatus as defined in claim 1, further comprising a load cell means associated with said pulling head for determining the magnitude of said cyclical tension loading to which said test specimens are subjected.

7. A method for simultaneously fatigue testing a plurality of test specimens having two ends by subjecting the specimens to cyclical tension loading to determine the fatigue strength limit of said plurality of test specimens, said method comprising:

providing a pressurized fluid source;

providing a pulling head having a block containing pressurized fluid passage means formed in the block for allowing pressurized fluid from said pressurized fluid source to be supplied to and exhausted from said pulling head;

providing a plurality of cylinders having two ends defined in said block of said pulling head, one of said two ends being in communication with said pressurized fluid passage means;

venting the other of said two ends to atmosphere;

providing a substantially cylindrical piston in each of said cylinders for movement towards said venting ends of said cylinders upon said pressurized fluid passge means being supplied pressurized fluid;

attaching one of said two ends of said test specimens to one of said pistons;

fixedly attaching the opposite ends of each said test specimen to a fixed point with respect to said movement of said plurality of pistons;

retaining each of said pistons within said pulling head upon said test specimens reaching said fatigue strength limit and breaking; and controlling the pressurized fluid to be alternately supplied to and exhausted from said pressurized fluid passage means in a manner that said plurality of pistons move towards and away from said fixed attached end of each specimen allowing said plurality of test specimens to be subjected to cyclical tension loading.

8. The method of claim 7 including counting the number of tension loading cycles to which each of said plurality of test specimens is subjected before reaching said fatigue strength limit.

9. The method of claim 7, including determining the magnitude of the tension loading to which said plurality of test specimens are subjected.

10. A fatigue testing apparatus for simultaneously subjecting a plurality of test specimens having two ends to cyclical tension loading to determine the fatigue strength limit of said plurality of test specimens, said fatigue testing apparatus comprising:

a pressurized fluid source;

a pulling head for applying a tension load to said test specimens, including:

(i) a top plate;

(ii) a center block having pressurized fluid passages defined therein for allowing pressurized fluid from said pressurized fluid source to be supplied and exhausted from said center block; said center block having a plurality of cylinders defined therein, each having two ends, one of said two ends being in fluid communication with said pressurized fluid passages and the other of said two ends having a vent to atmosphere defined therein; said top plate integral with said center block and having said vent to atmosphere defined therein corresponding to each of said plurality of cylinders;

(iii) a bottom plate integral with said center block, said bottom plate having defined therein a piston rod receiving opening corresponding to each of said plurality of cylinders;

a plurality of substantially cylindrical pistons carried in said cylinders for movement therein towards said vent upon said pressurized fluid passages being supplied pressurized fluid, each of said pistons having a piston rod extending outwardly therefrom through a said piston rod receiving opening defined in said bottom plate;

test specimen attachment means for attaching one of said two ends of each of said plurality of test specimens to each of said plurality of pistons;

fixed attachment means opposite said test specimen attachment means for fixedly attaching the other of said two ends of each of said plurality of test specimens with respect to said movement of said plurality of pistons; and control means for allowing pressurized fluid to be alternately supplied to and exhausted from said pressurized fluid passages, thereby allowing said plurality of pistons and said test specimen attachment means associated therewith to move towards and away from said fixed attachment means; said movement of said test specimen attachment means towards and away from said fixed attachment means allowing said plurality of test specimens to be subjected to cyclical tension loading.

11. The fatigue testing apparatus as defined in claim 10, wherein said test specimen attachment means and said fixed attachment means comprises threaded couplings.

12. The fatigue testing apparatus as defined in claim 10, wherein said test specimen attachment means and said fixed attachment means comprises clevis pin couplings.

13. The fatigue testing apparatus as defined in claim 10, further comprising seal means associated with said plurality of pistons for preventing pressurized fluid from passing from said pressurized fluid passage means to a said vent.

14. The fatigue testing apparatus as defined in claim 10, further comprising counter means associated with said plurality of test specimens for determining the number of tension load cycles to which said plurality of test specimens are subjected before exceeding said fatigue strength limit.

15. The fatigue testing apparatus as defined in claim 1, further comprising load measuring means associated with said pulling head for determining the tension load applied by said pulling head to said plurality of test specimens.

* * * * *